United States Patent [19]

Metz et al.

[11] Patent Number: 4,505,914

[45] Date of Patent: Mar. 19, 1985

[54] PHARMACEUTICAL FOR THE TREATMENT OF SLEEP DISORDERS

[75] Inventors: Gunter Metz, Blaubeuren; Kurt Rauchle, Blaubeuren-Sonderbuch, both of Fed. Rep. of Germany

[73] Assignee: Merckle GmbH, Blaubeuren, Fed. Rep. of Germany

[21] Appl. No.: 518,394

[22] Filed: Jul. 29, 1983

[30] Foreign Application Priority Data

Jul. 29, 1982 [DE] Fed. Rep. of Germany ....... 3228351

[51] Int. Cl.³ .......................................... A61K 31/495
[52] U.S. Cl. ..................................................... 514/255
[58] Field of Search ....................................... 424/250

Primary Examiner—Stanley J. Friedman
Attorney, Agent, or Firm—Michael N. Meller

[57] ABSTRACT

At least one barbiturate or one of its pharmaceutically acceptable salts is combined with cinnarizine or flunarizine or one of their pharmaceutically acceptable salts to provide a hypnotic requiring lower dosages of barbiturates to produce the same effect as the barbiturate alone.

19 Claims, No Drawings

PHARMACEUTICAL FOR THE TREATMENT OF SLEEP DISORDERS

BACKGROUND OF THE INVENTION

The invention relates to a pharmaceutical for the treatment of sleep disorders, which contains lower dosages of barbiturates in combination with cinnarizine and/or flunarizine.

Among the therapeutically employed hypnotics, barbiturates still hold a central position today. Among the disadvantages of their use is, among others, the need of a higher dosage, which, depending upon the barbiturate, requires single doses of 150 mg to about 650 mg. In the literature, different materials are known which can increase the effect of barbiturates. Thus, Dimercaprol (BAL) checks the decomposition of pentobarbital [J. Pharmacol. Exp. Therap. 109, 292 (1953)], also tocopherol increases the effect of barbiturates [Arch. Int. Pharmacodyn. Therap. 97, 473 (1954)]. In addition it is known that strong antihistamines (phenothiazines) and tranquilizers (Meprobamate), have a pontentiating or enhancing effect on barbiturates. Under the usual combinations of barbiturates with sedatives and other hypnotics, which are registered in the list of traded drugs in Germany, there are still few representatives of these two groups.

SUMMARY OF THE INVENTION

It has now been surprisingly found that cinnarizine and flunarizine have a potentiating or enhancing effect on the action of barbiturates and these combinations have new pharmacological properties. Cinnarizine (1-benzhydryl-4-trans-cinnamylpiperazine or 1-cinnamyl-4-diphenylmethylpiperazine) is known from German Pat. No. 1,086,235. Cinnarizine and also its difluorinated structural analog, flunarizine, have only weak antihistaminic properties and are used therapeutically as peripheral and cerebral vasodilators.

According to the invention there is provided a pharmaceutical characterized in that, besides the usual pharmaceutical adjuvants and carriers, it contains, as the active ingredient, a combination of (a) one or more compounds from the group of barbiturates and their pharmaceutically acceptable salts and (b) cinnarizine or flunarizine or a pharmaceutically acceptable salt of these compounds.

The pharmaceutical according to the invention is outstandingly suitable for the treatment of sleep disorders.

DETAILED DESCRIPTION

Typical representatives of the group of barbiturates are phenobarbital, cyclobarbital-calcium and/or hexobarbital.

Suitably the pharmaceuticals according to the invention contain components a(barbiturate) and b(cinnarizine or flunarizine) in a weight ratio of a:b from 100:1 to 5:1, preferably, from 50:1 to 10:1. Preferably the pharmaceuticals according to the invention are formulated for oral and rectal application. Each unit dose of the pharmaceutical according to the invention contains suitable 100–150 mg of the barbiturate component (a) and 5–15 mg cinnarizine ($b_1$) or 2–5 mg flunarizine ($b_2$).

In general, the weight ratio of barbiturate (a) to cinnarizine ($b_1$) is 30:1 to 5:1, preferably 20:1 to 10:1, and the weight ratio of barbiturate (a) to flunarizine ($b_2$) is 100:1 to 20:1, preferably 50:1 to 30:1.

The effect of cinnarizine and flunarizine on the prolongation of sleeping time was determined on male NMRJ mice modified according to "Screening Methods in Pharmacology", R. A. Turner, 1976, page 70. A typical representative from the group of barbiturates with long action (phenobarbital), with short to average action (cyclobarbital-calcium) as well as ultra short action (hexobarbital) as well as a combination of two barbiturates (cyclobarbital-calcium + hexobarbital) was applied orally in graduated doses. The dose required for a 30-minute sleeping period was calculated as the $ED_{50}$. In further tests, the animals were given the respective $ED_{50}$ as the sleep inducing basic dose as well as cinnarizine or flunarizine in graduated dosages. For the combination, the $ED_{50}$ was calculated by probit analysis, whereby the respective dosages of cnnarizine or flunarizine were selected so that the onset of sleeping time was increased by 50%. The results of these tests are set forth in Tables 1 and 2.

In a further experiment, the influence of cinnarizine on barbiturates on the measured parameters of sleep duration, prolongation of sleeping time, $ED_{50}$, as well as the onset of the effect and the optimum effect were tested. The results of this experiment are given in Table 3.

As a criterium for the onset of the effect, the beginning of the excitation stage was measured. For the optimum effect, the beginning of the sleep phase was tested every 10 minutes by the tail and corneal reflex (according to Irvin) according to the following designations:

```
  0 = normal reaction
 −1 = slightly lessened
 −2 = clearly lessened          ⎫
 −3 = highly lessened           ⎬ Optimum effect
 −4 = complete lack of reaction ⎭
```

The results of the sleep duration and the sleeping time prolongation in Table 3 confirm the results of the previous experiments (Table 2). A corresponding synergistic effect is confirmed for the onset of the effect as well as for the optimum effect. Obviously there is also a specific barbiturate effect. In the case of hexobarbital, cinnarizine shows the highest potency, whereas for cyclobarbital-calcium, flunarizine shows the highest potency.

The combination of both barbiturates requires, for cinnarizine as well as for flunarizine, higher dosages to obtain an $ED_{50}$ in comparison with the individual barbiturates. The onset of the effect in comparison with the control is not changed with the combination, as it is for the individual barbiturates. Here the marked effect of cyclobarbital-calcium is confirmed.

From the results in Tables 1 to 3, it is concluded that a mixture of cinnarizine or flunarizine with barbiturates produces a marked prolongation of the sleeping time, whereby, to obtain an equivalent effect, considerably lower dosages of the barbiturates are possible. It also produces a considerable improvement in the onset of the effect and of the optimum effect.

The pharmaceuticals according to the invention are dispensed rectally in the form of suppositories and rectal capsules and orally in the form of tablets, capsules or dragees with the use of conventional pharmaceutically acceptable aids as well as necessary carriers, lubricants and disintegrants.

EXAMPLES

1. Hard Gelatin Capsules

| | |
|---|---|
| Cyclobarbital - Ca | 100.0 mg |
| Flunarizine | 5.0 mg |
| Lactose | 80.0 mg |
| Magnesium Stearate | 2.0 mg |
| Talc | 8.0 mg |
| Polyvinylpyrrolidone | 5.0 mg |
| Corn Starch | 30.0 mg |

2. Tablets

| | |
|---|---|
| Hexobarbital | 50.0 mg |
| Cyclobarbital - Ca | 100.0 mg |
| Cinnarizine | 15.0 mg |
| Hydroxypropylcellulose | 15.0 mg |
| Microcrystalline cellulose | 103.0 mg |
| Gelatine | 5.5 mg |
| Stearic Acid | 1.5 mg |
| Talc | 5.0 mg |

3. Suppositories

| | |
|---|---|
| Hexobarbital | 150.0 mg |
| Cinnarizine | 10.0 mg |
| Suppository Base | 1890.0 mg |

TABLE 1

Determination of the oral $ED_{50}$ of the barbiturates using 10 male NMRτ mice/group

| Barbiturate | Dose mg/kg | Sleep Time Min. | $ED_{50}$ mg/kg |
|---|---|---|---|
| Phenobarbital | 200 | 4.29 | 256 |
| | 250 | 27.52 | |
| | 300 | 49.06 | |
| | 400 | 49.28 | |
| Hexobarbital | 250 | 3.03 | 710 |
| | 500 | 16.52 | |
| | 750 | 32.53 | |
| | 1000 | 56.08 | |
| Cyclobarbital-Ca | 100 | — | 239 |
| | 200 | 14.01 | |
| | 250 | 34.38 | |
| | 300 | 90[(1)] | |
| Cyclobarbital-Ca + | 150 | 8.64 | 225 |
| Hexobarbital | 200 | 21.05 | |
| (40 + 30) | 250 | 41.09 | |
| | 400 | >90.0[(2)] | |

[(1)] 8 animals showed 90 min., 2 animals 60.5 and 53.3 min.
[(2)] 2 animals had a sleep time of 67.60 and 66.90 min., the rest >90 min.

TABLE 2

Determination of the sleeping time prolongation under the influence of cinnarizine and flunarizine ($ED_{50}$) 10 male NMRτ mice/group

| | | Cinnarizine | | | Flunarizine | | |
|---|---|---|---|---|---|---|---|
| Barbiturate | Dose mg/kg | Dose mg/kg | Sleep Time Min. | $ED_{50}$ mg/kg | Dose mg/kg | Sleep Time Min. | $ED_{50}$ mg/kg |
| Phenobarbital | 256 | — | 22.34 | | | | |
| | 256 | 1 | 25.78 | 3.57 | | | |
| | 256 | 5 | 32.85 | | | | |
| | 256 | 10 | 43.55* | | | | |
| Hexobarbital | 710 | — | 32.74 | | — | 38.78 | |
| | 710 | 0.5 | 35.37 | 0.75 | 1.0 | 40.44 | 2.94 |
| | 710 | 0.75 | 43.93** | | 2.5 | 45.17 | |
| | 710 | 1.0 | 65.58** | | 5.0 94.51*** | | |
| Cyclobarbital-Ca | 239 | — | 27.45 | | — | 32.03 | |
| | 239 | 1.0 | 24.34 | 2.77 | 0.25 | 39.54 | 0.38 |
| | 239 | 2.5 | 41.43* | | 1.0 | 62.67*** | (0.29–0.45) |
| | 239 | 5.0 | 49.99** | | 2.5 | 75.15*** | |
| Cyclobarbital-CA + | 225 | — | 34.27 | | — | 33.07 | |
| Hexobarbital | 225 | 1.0 | 31.09 | 4.68 | 2.5 | 33.45 | 7.52 |
| (40 + 30) | 225 | 2.5 | 37.92 | | 10.0 | 56.49** | (6.85–8.30) |
| | 225 | 5.0 | 53.22* | | 15.0 | 65.12*** | |

*p <0.05
**p <0.01
***p <0.001

TABLE 3

Sleeping Time, Onset of Effect and Optium Effect under the influence of cinnarizine on 10 male NMRτ mice/group

| Barbiturate | Dose mg/kg | Cinnarizine | Sleep Time Min. | % | $ED_{50}$[(2)] mg/kg | Onset x Min. | p.a. % | Min. | Optimum Reflex | %[(1) (2)] |
|---|---|---|---|---|---|---|---|---|---|---|
| Hexobarbital | 710 | —(C) | 35.86 | 100.0 | | 2.89 | 100.0 | 10–20 | −1 | 100.0 |
| | 710 | 0.50 | 40.66 | 113.4 | 0.77 | 2.49 | 86.2 | 10–30 | −3 | 278.2–336.0 |
| | 710 | 0.75 | 42.38 | 118.2 | | 2.22 | 76.8 | 10–20 | −3 | 263.2–203.0 |
| | 710 | 1.00 | 76.14 | 212.3 | | 1.59 | 55.0 | 10–30 | −4 | 300.8–407.0 |
| Cyclobarbital calcium | 239 | —(C) | 24.64 | 100.0 | | 4.27 | 100.0 | 10 | 0/−1 | 100.0 |
| | 239 | 1.0 | 26.21 | 106.4 | 3.52 | 2.19 | 51.3 | 10 | −1 | 166.7 |
| | 239 | 2.5 | 31.08 | 126.1 | (3.07–4.21) | 2.31 | 54.1 | 10–30 | −1 | 350.0 |
| | 239 | 5.0 | 42.49 | 172.4 | | 2.54 | 59.5 | 10 | −2 | 350.0 |
| Cyclobarbital calcium + Hexobarbital (40 + 30) | 225 | —(C) | 35.01 | 100.0 | | 1.15 | 100.0 | 10–20 | −1/−2 | 100.0 |
| | 225 | 1.0 | 32.42 | 92.6 | 4.94 | 1.09 | 94.8 | 10–20 | −2 | 156.3–183.3 |
| | 225 | 2.5 | 38.65 | 110.4 | (4.19–6.49) | 1.18 | 102.6 | 10–20 | −2 | 138.8–177.5 |
| | 225 | 5.0 | 54.82 | 156.6 | | 1.18 | 102.6 | 10–40 | −2/−3 | 175.0–233.0 |

(1) % value calculated on each barbiturate without cinnarizine (C)
(2) where there were strong differences among individuals the entire range (min./max. confidence interval) is given

I claim:

1. A pharmaceutical composition for treatment of sleep disorders comprising a pharmaceutically effective amount of a combination of
   (a) at least one compound selected from the group consisting of barbiturates and their pharmaceutically acceptable salts and
   (b) a compound selected from the group consisting of cinnarizine, flunarizine and their pharmaceutically acceptable salts, wherein the weight ratio of (a) to (b) is 100:1 to 5:1.

2. The composition according to claim 1, wherein the barbiturate is at least one selected from the group consisting of phenobarbital, cyclobarbital-calcium and hexobarbital.

3. The composition according to claim 1, wherein the weight ratio is 50:1 to 10:1.

4. The composition according to claim 2, wherein the weight ratio of (a) to (b) is 100:1 to 5:1.

5. The composition according to claim 4, wherein the weight ratio is 50:1 to 10:1.

6. The composition according to claim 1, wherein (b) is cinnarizine or one of its pharmaceutically acceptable salts and the weight ratio of (a) to (b) is 30:1 to 5:1.

7. The composition according to claim 7, wherein the weight ratio is 20:1 to 10:1.

8. The composition according to claim 2, wherein (b) is cinnarizine or one of its pharmaceutically acceptable salts and the weight ratio of (a) to (b) is 30:1 to 5:1.

9. The composition according to claim 8, wherein the weight ratio is 20:1 to 10:1.

10. The composition according to claim 1, wherein (b) is flunarizine or one of its pharmaceutically acceptable salts and the weight ratio of (a) to (b) is 100:1 to 20:1.

11. The composition according to claim 10, wherein the weight ratio is 50:1 to 30:1.

12. The composition according to claim 2, wherein (b) is flunarizine or one of its pharmaceutically acceptable salts and the weight ratio of (a) to (b) is 100:1 to 20:1.

13. The composition according to claim 12, wherein the weight ratio is 50:1 to 30:1.

14. The composition according to claim 8, wherein (a) is hexobarbital.

15. The composition according to claim 9, wherein (a) is hexobarbital.

16. The composition according to claim 12, wherein (a) is cyclobarbital-calcium.

17. The composition according to claim 13, wherein (a) is cyclobarbital-calcium.

18. The composition according to claim 1, which is formulated for oral or rectal application.

19. The composition according to claim 1, wherein the unit dosage is 100–150 mg of (a).

* * * * *